United States Patent [19]

Wong

[11] Patent Number: 4,647,779
[45] Date of Patent: Mar. 3, 1987

[54] MULTIPLE LAYER POSITRON EMISSION TOMOGRAPHY CAMERA

[75] Inventor: Wai-Hoi Wong, Houston, Tex.

[73] Assignee: Clayton Foundation For Research, Houston, Tex.

[21] Appl. No.: 734,012

[22] Filed: May 13, 1985

[51] Int. Cl.⁴ .............................. G01T 1/20; G01T 1/64
[52] U.S. Cl. ................................ 250/363 R; 250/367; 250/363 S
[58] Field of Search ............... 250/363 SA, 363 SB, 250/367, 363 S, 336, 366; 378/4, 5

[56] References Cited

U.S. PATENT DOCUMENTS

| | | | |
|---|---|---|---|
| 3,970,853 | 7/1976 | Kuhl et al. | 250/363 SB |
| 4,029,963 | 6/1977 | Alvarez et al. | 378/5 |
| 4,153,839 | 5/1979 | Hounsfield et al. | 250/367 |
| 4,247,774 | 1/1981 | Brooks | 250/367 |
| 4,445,226 | 4/1984 | Brody | 378/5 |
| 4,473,749 | 9/1984 | Derenzo et al. | 250/363 SB |
| 4,511,799 | 4/1985 | Bjorkholm | 250/367 |
| 4,563,582 | 1/1986 | Mullani | 250/363 SA |

Primary Examiner—Carolyn E. Fields
Assistant Examiner—David P. Porta
Attorney, Agent, or Firm—Fulbright & Jaworski

[57] ABSTRACT

A positron emission tomography camera having a patient area with a plurality of fixed detector rings positioned side by side around the patient area to detect radiation. Each ring contains a plurality of scintillation detectors directed toward the patient area for defining a plane slice. Each ring includes multiple layers of scintillation detectors in which the detectors in one of the layers is offset relative to the detectors in the other layers in a ring for increasing the sampling of detected radiation. Photo multipliers for converting detected radiation into electrical pulses are positioned adjacent each ring but offset from the plane of each ring and are directed perpendicularly to the plane of the adjacent ring. The depth of each ring is sufficient to stop gamma radiation but the depth of each layer is less whereby image resolution is improved.

9 Claims, 11 Drawing Figures

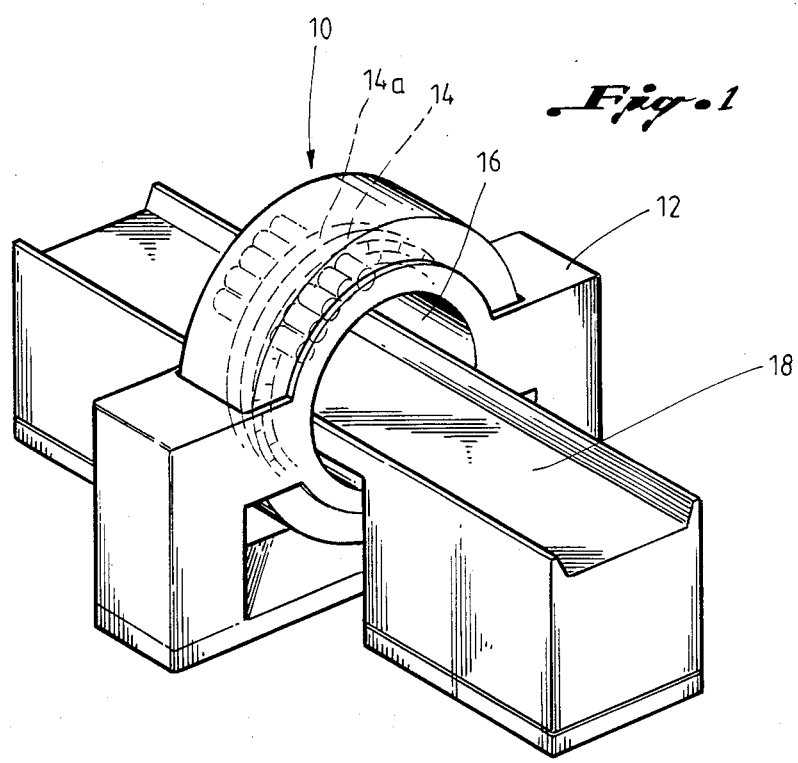
Fig. 1
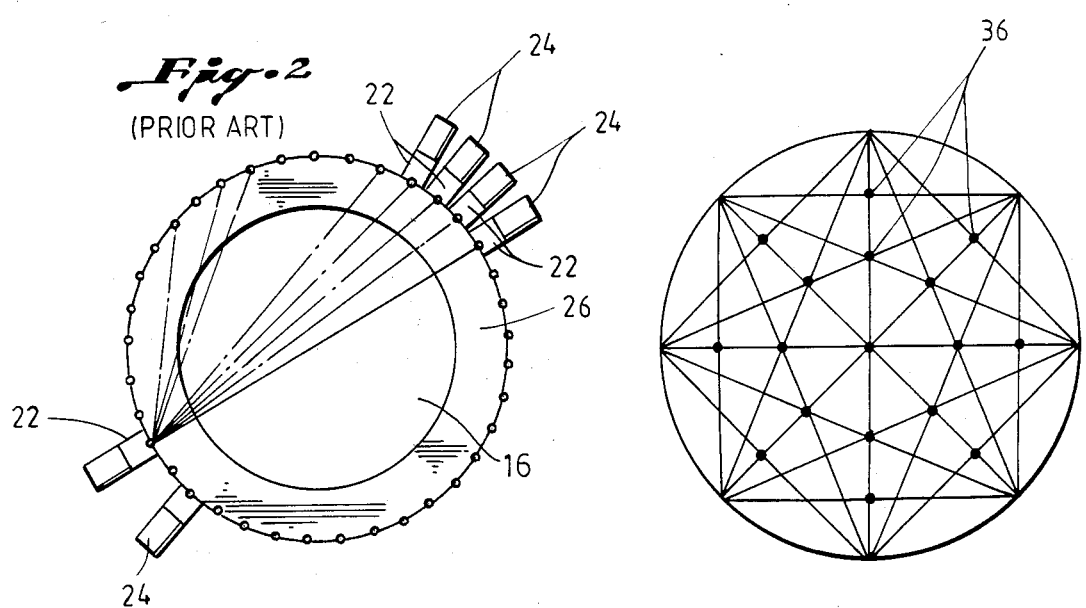
Fig. 2 (PRIOR ART)
Fig. 3 (PRIOR ART)

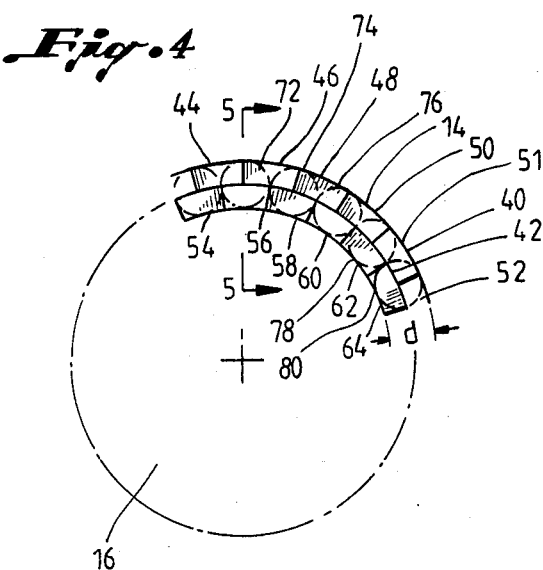
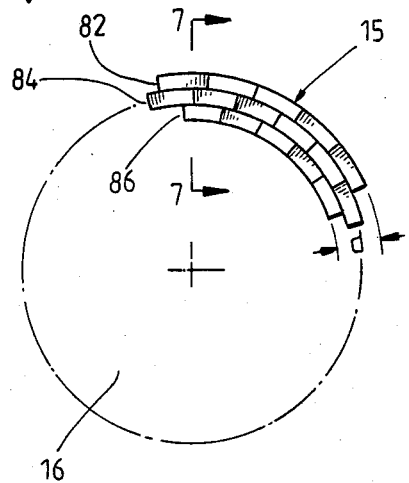
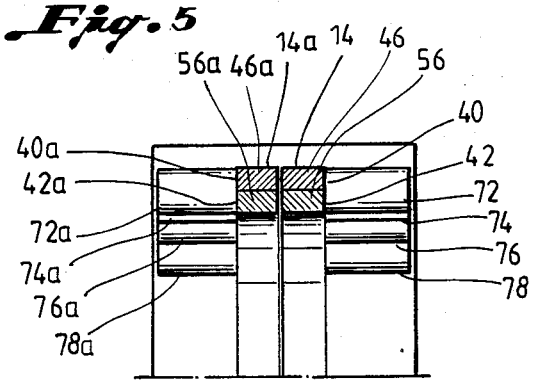
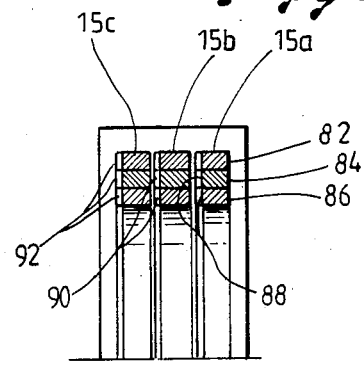
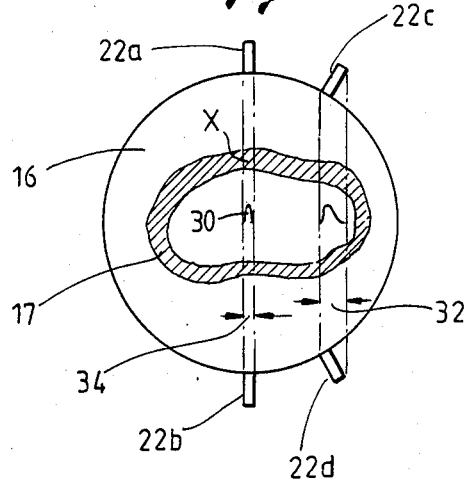
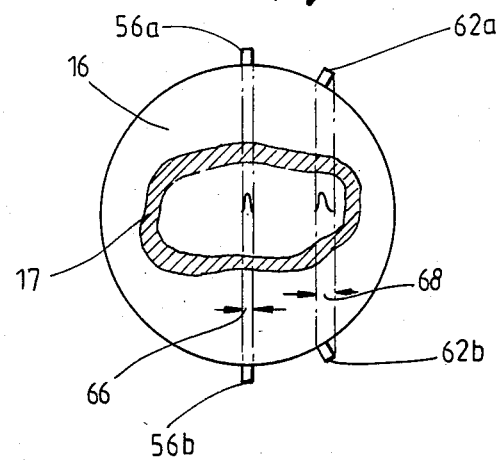

MULTIPLE LAYER POSITRON EMISSION TOMOGRAPHY CAMERA

BACKGROUND OF THE INVENTION

The value of the positron emission tomography camera for allowing in vivo regional quantitative measurement of biochemistry and function in organs of animals and humans is well known as set forth in patent application Ser. No. 396,098, filed July 7, 1982, entitled Three-Dimensional Time-of-Flight Positron Emission Camera System, and patent application Serial No. 613,699, filed May 24, 1984, entitled Positron Emission Tomography Camera.

Conventional positron cameras are extremely expensive, the intrinsic resolution for off-center points is degraded, and the cameras of conventional design require wobbling of the detector ring in order to obtain adequate sampling, which requires expensive and complicated equipment and controls.

The present invention is directed to a positron emission camera (PET) which will provide a small, inexpensive, highly sensitive, motionless camera of greater image sharpness than is provided by conventional designs.

The present invention is directed to a positron emission tomography camera having multiple layers of scintillators with each layer staggered from its adjacent layer. The thickness of each detector is less than that of a conventional detector and allows an improvement in the resolution. The structure reduces the angulation degradation thereby allowing the diameter of the detector ring to be reduced which in turn increases the camera sensitivity and reduces detector costs. The multiple layers of staggered detectors greatly increases the number of samples detected and allows the elimination of the wobble function from the camera.

Another object of the present invention is the provision of a PET camera having a patient area, and a plurality of detector rings positioned side by side around the patient area to detect radiation from a patient in the patient area. Each ring contains a plurality of scintillation detectors directed toward the patient area for defining a plane slice through the patient area by the detectors in each ring. Each ring includes multiple layers of scintillation detectors, the detectors in one of the layers being offset relative to the detectors in the other layers in a ring. Means for converting the detected radiation into electrical pulses is provided adjacent each ring but offset from each ring. The means are directed perpendicular to the plane of the adjacent rings.

Still another object of the present invention is wherein the converting means may be tube photomultipliers or silicon avalanche photomultipliers.

Still a further object of the present invention is wherein the depth of each ring of the detector is sufficient to stop radiation but the depth of each layer of the ring is less than the depth of the ring whereby the angular degradation of the image resolution is reduced.

Other and further objects, features and advantages will be apparent from the following description of a present preferred embodiment of the invention, given for the purpose of disclosure and taken in conjunction with the accompanying drawings.

BRIEF DESCRIPTION OF THE DRAWINGS

FIG. 1 is a perspective elevational view of the positron emission tomograph camera of the present invention, FIG. 2 is a schematic elevational view, in cross section, illustrating the imaging of plane slices in a conventional positron camera, FIG. 3 is a schematic cross-sectional view of the sampling of points in a conventional PET camera utilizing eight detectors, FIG. 4 is a schematic cross-sectional view of the positron emission tomography camera of the present invention, FIG. 5 is a cross-sectional view taken along the line 5—5 of FIG. 4, FIG. 6 is a schematic elevational view, in cross section, of another embodiment of the placement of the detectors in the invention of the present invention, FIG. 7 is a cross-sectional view, taken along the line 7—7 of FIG. 6, FIG. 8 is a schematic elevational view in cross section illustrating the point spread function in a conventional prior art camera, FIG. 9 is a view similar to that of FIG. 8 utilizing the smaller depth detectors of the present invention.

DESCRIPTION OF THE PREFERRED EMBODIMENT

Figure 10:
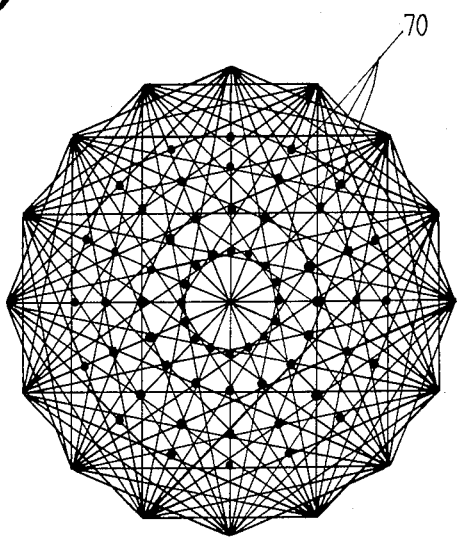
FIG. 10 is a graph illustrating the sampling points obtained by the present invention using two multiple layers of eight detectors each.

Referring now to the drawings, particularly to FIG. 1, the reference numeral 10 indicates a positron emission tomography (PET) camera having a support or gantry 12, a plurality of detector rings here shown as two rings 14 and 14a for convenience, positioned side by side around and surrounding a patient area 16 to detect radiation therefrom. The patient area 16 may include a patient bed 18 for supporting a patient and the patient area opening 16 may be tilted and the bed 18 rotated for scanning the body over an organ from several different positions.

In a PET camera, a positron isotope, such as 82 Rb, is injected into the patient. Each positron isotope atom then emits two gammas simultaneously and back-to-back. The detectors (scintillator crystals such as bismuth germante (BGO)) then capture these gammas to produce the image of the tracer distribution.

Referring now to FIG. 2, a cross-section of a typical PET camera has an opening 16 for insertion of the patient to be scanned, a plurality of scintillator crystal detectors 22 in each detector ring which are mounted around the patient area and a plurality of photo multiplier tubes 24 for converting the detected radiation into electrical pulses. Extending inwardly from the ring 14 of detectors 22 on either side of the detectors 22 are septa 26 for reducing unwanted signals such as random and scattered signals. While PET cameras allow in vivo regional quantitative measurement of biochemistry and functions in human and animal organs, presently the complexity, sensitivity and cost of PETS restrict their widespread use in both clinical and research laboratories. At the present time, the cost of a sophisticated PET camera may be nearly two million dollars.

Figure 11:
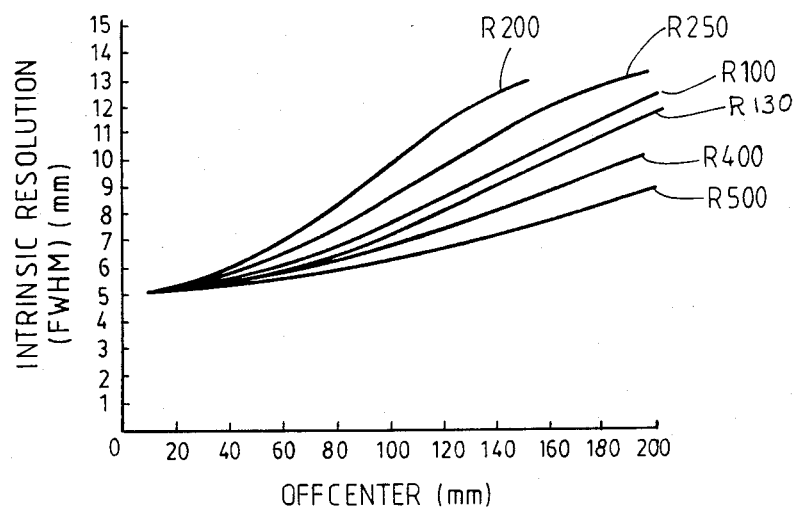
FIG. 11 is a graph illustrating image resolution degradation of points away from the center of the field of view in conventional PET cameras.

All imaging devices create a blurred image of the original object. The degree of blurring (resolution) for each imaging device can be characterized by its image as a source point. Referring now to FIG. 8, a prior art PET camera is schematically shown surrounding a patient area 16 for detecting radiation from a patient 17 by means of detectors 22a, 22b, 22c and 22d. A point source will be imaged, not as a point source, but as a more spread-out bell-shaped function 30. Furthermore, the detector size limits the accuracy of determining the emission sites. That is, the detectors 22a and 22b cannot delineate whether the event which it is detecting is from X or Y. A high resolution (sharpness) imaging device has a narrow point spread function which allows the delineation of finer details. The present design has several fundamental difficulties. The first is the worsening of the image sharpness (intrinsic resolution) for off-center points. The off-center pair of detectors 22c and 22d looking at an off-center point is tilted at an angle. This makes the detectors 22c and 22d appear to be wider for gammas penetrating the neighbors of detectors 22c and 22d and result in a wider point spread function. That is, the off-center detectors 22c and 22d detect a wider point spread function 32 as compared to the point spread detection 34 for the on-center detectors 22a and 22b. This angulation degradation and resolution (sharpness) worsens as the diameter of the detector rings 14 gets smaller. The applicant has calculated this angulation degradation and resolution which results are shown in FIG. 11. These results show that even with a relatively small object such as a dog (roughly 100 mm. radius object), the resolution degradation is severe unless the detector ring radius is larger than 400–500 mm. A larger detector ring radius decreases the sensitivity greatly because the detectors are further away from the object. That is, the camera sensitivity equals 1/R where R is the radius of the ring of detectors 22. Furthermore, a large detector ring increases the detector cost as the number of detectors required is greatly increased.

Another problem with the conventional design is the need for wobbling or movement of the detectors 22 to obtain an get adequate sampling of the object. That is, referring to FIG. 3 of a prior art PET camera, the existing design with eight detectors 22 will provide detection of seventeen sampling points 36. This is not a sufficient sampling as the required Nyquist sampling theorem requires that the radial sampling should be half the size of the intrinsic resolution otherwise there will be ring artifacts in the image. Therefore, in order to wobble the detectors 22, present PET cameras utilize an expensive mechanical drive system to move the entire ring of detectors 22 continuously on a small eccentric circular track to cover or sample more spots during the imaging procedure. This solution requires a sophisticated mechanical drive and electronics for data handling to keep track of the position of the detectors continuously and finding the count according to the instantaneous position of each detector.

Referring now to FIGS. 1, 4 and 5, the present invention is directed to a PET camera having a plurality of rings, such as 14 and 14a, positioned side by side around the patient area 16 to detect radiation from a patient. Each ring 14 and 14a includes multiple layers of scintillation detectors such as layers 40 and 42 in ring 14 and 40a and 42a in ring 14a in which the detectors in one of the layers is offset relative to the detectors in the other layer in the same ring. Thus, layer 40 includes a plurality of detectors 44, 46, 48, 50, 51, 52, etc. Similarly, ring 42 includes a plurality of detectors 54, 56, 58, 60, 62, 64, etc. The total combined depth d of the two layers 40 and 42 of the detectors is approximately equal to the depth of each detector in the existing mono-layered conventional detector systems. Since the combined detector depth d for stopping the gammas is the same as in the conventional design, the gamma stopping power or total detection efficiency does not change. However, the depth of each layer 40 and 42 in the new design is less than that of a conventional design, preferably 50% less. This reduced depth reduces the angular degradation of image resolution. That is, referring to FIG. 9, utilizing the design, the detectors 56a and 56b which are diametrically opposed measure a point spread function 66 equal to the point spread function 34 of the conventional design shown in FIG. 8. However, the off-center detectors such as 62a and 62b, since they have a depth of approximately one-half of the conventional detectors 22c and 22d of FIG. 8, have a point spread function 68 which is less than the point spread function 32 of the detectors 22c and 22d of the conventional detector shown in FIG. 8 and therefore the angular degradation of image resolution at the off-center detectors is reduced. Since the angulation degradation is reduced, the radius of the detector rings 14 can be reduced from that of the conventional arrangement of FIGS. 2 and 8. (Normally PET cameras have to increase the radius in order to reduce angulation degradation). The reduction in the detector ring radius increases the camera sensitivity, sensitivity is equal to 1/R, as the detectors are now closer to the object. For example, with a dog cross-sectional radius of 10 cm., the detector ring radius can be made to be as small as 15 cm. With a two-layer design 40 and 42 of FIGS. 4 and 5, with the detectors (5 mm. wide), the resolution is calculated to be 2.6 mm. and 4.8 mm. at the center and 10 mm. off radius, respectively. However, with a conventional monolayered design, similar resolution can only be achieved with a ring radius of 28 cm. Hence the sensitivity is improved by two times (28/15) by the reduction of the detector ring radius from 28 cm. to 15 cm. In addition, the total volume of detector crystals used is also reduced by two times because of the smaller detector ring radius. Hence, the present design increases the sensitivity and reduces the detector cost. In addition to cutting the total mass (cost) of detection scintillators for the camera, the cost per unit mass also goes down with the smaller crystals because several detector crystals are cut from one larger grown crystal ingot. The percentage of waste for each ingot decreases with the smaller cutting.

Referring now to FIG. 10, a chart of the sampling points 70 of the present design is shown using eight detectors in the outer layer 40 and eight detectors in the inner layer 42 to provide sixty-four sampling points. In the present invention, the detectors in the layers 40 and 42 are fixed and do not require wobbling, but supply a sufficient number of sampling points to satisfy the Nyquist sampling theorem whereby ring artifacts will be minimized and the expensive mechanic drive system, the electronics to keep track of the position of the moving detectors, the more complex reconstruction algorithm and the possibility of gated cardiac image artifacts (patient heartbeats) with the detector movement frequency (closed) are all eliminated.

In order to measure which of the various detectors in the multiple rings 40 and 42 are detecting the radiation from the patient, a plurality of means for converting the detected radiation into electrical impulses are provided such as photo multiplier tubes 72, 74, 76, 78, and 80, etc. for ring 14 of detectors and tubes 72a, 74a, 76a, etc. for ring 14a. Because the rings 14 and 14a contain multiple layers 40 and 42 and 40a and 42a, the multiplier tubes are positioned adjacent each of the rings 14 and 14a but offset from the plane of each ring 14 and 14a and are directed perpendicularly to the plane of the adjacent ring. Thus multiplier tube 72 is positioned adjacent layers 40 and 42 and multiplier tube 72a is adjacent layers 40a and 42a. While the various photo multiplier tubes provide an excellent and low cost device for converting the detected radiation into electrical pulses, they are quite bulky and therefore their use limits the present camera to having two rings 14 and 14a as the rings must be closely adjacent to each other to provide closely adjacent plane slices through the patient.

Referring now to FIGS. 6 and 7, a ring 15a is shown having three layers 82, 84 and 86. As best seen in FIG. 7, more than two rings can be provided such as rings 15a, 15b and 15c. Adjacent each of the rings and directed perpendicularly to the plane of the adjacent rings are a plurality of silicon avalanche photodiodes 88, 90 and 92. This type of photodiodes has the advantage of being small enough so that more than two rings of detectors may be utilized to provide a multiplicity of adjacent plane slices through a patient. A disadvantage of the silicon avalanche photomultipliers is their high cost.

The present design will provide a small, high sensivity, high resolution, simple and low cost PET camera. The important advantages are:

(1) the sensivity will increase by two times or more with a smaller (half size) detector ring radius which allows imaging time to be shortened by half, (2) the total volume or mass of detection material will be reduced by half which represents a significant savings in cost, (3) the elimination of the detector ring wobbling motion will drastically reduce the mechanical complexity, electronic and data handling complexity, (4) the present design provides an improved solution to the detector angulation.

The present invention, therefore, is well adapted to carry out the objects and attain the ends and advantages mentioned as well as others inherent therein. While present preferred embodiments of the invention have been given for the purposes of disclosure, numerous changes in the details of construction and arrangement of parts may be made without departing from the spirit of the invention and the scope of the appended claims.

What is claimed is:

1. A positron emission camera tomography camera comprising, a patient area, a plurality of detector rings positioned side by side around the patient area to detect radiation from opposite sides of a patient in the patient area, each ring containing a plurality of scintillation detectors directed towards the patient area for defining a plane slice through the patient area by the detectors in each ring, each ring including multiple layers of scintillation detectors, the detectors in one of the layers being offset relative to the detectors in the other layers in the same ring, and means for converting detected radiation into electrical pulses, said means positioned adjacent each ring but offset from each ring, said means directed perpendicular to the plane of the adjacent ring.

2. The apparatus of claim 1 wherein the converting means are photomultiplier tubes, each of which detects radiation from at least two layers of detectors.

3. The apparatus of claim 1 wherein the converting means are silicon avalanche photodiodes.

4. The apparatus of claim 1 the depth of each ring is sufficient to stop radiation, but the depth of each layer is less than the depth at which the angulation degradation of image resolution is reduced.

5. The apparatus of claim 1 wherein each ring includes two layers of detectors.

6. The apparatus of claim 1 wherein each ring includes three layers of detectors.

7. A positron emission tomography camera comprising, a patient area, a plurality of fixed circular detector rings positioned side by side around the patient area to detect radiation from opposite sides of a patient in the patient area, each ring containing a plurality of scintillation detectors directed towards the patient area for defining a plane slice through the patient area by the detectors in each ring, said detectors on opposite sides of the patient detecting two oppositely directed gamma rays, each ring including multiple layers of scintillation detectors, the detectors in one of the layers being offset relative to the detectors in the other layers in a ring for increasing the sampling of detected radiation, the depth of each ring being approximately equal to the depth of conventional mono-layered detectors and the depths of each layer being approximately equal, and means for converting detected radiation into electrical pulses, said means positioned adjacent each ring but offset from the plane of each ring, said means directed perpendicularly to the plane of the adjacent ring.

8. The apparatus of claim 7 wherein the converting means are photomultiplier tubes each of which detects radiation from more than one layer of detectors.

9. The apparatus of claim 7 wherein the scintillation detectors of each layer are of the same material.

* * * * *